US006601247B2

(12) United States Patent
Shimizu

(10) Patent No.: US 6,601,247 B2
(45) Date of Patent: Aug. 5, 2003

(54) LIGHT TRANSMITTING TYPE BATHTUB

(76) Inventor: Hideo Shimizu, 26-26, Minami-Otsuka 1-Chome, Toshima-Ku, Tokyo (JP)

( * ) Notice: Subject to any disclaimer, the term of this patent is extended or adjusted under 35 U.S.C. 154(b) by 0 days.

(21) Appl. No.: 10/179,596

(22) Filed: Jun. 24, 2002

(65) Prior Publication Data
US 2003/0019028 A1 Jan. 30, 2003

(30) Foreign Application Priority Data

Jul. 30, 2001 (JP) ........................................ 2001-229531

(51) Int. Cl.[7] ................................................ A47K 3/02
(52) U.S. Cl. ................................... 4/584; 4/538; 4/546
(58) Field of Search ............................ 4/487, 538, 539, 4/541.1, 546, 584, 580, 506, 661

(56) References Cited

U.S. PATENT DOCUMENTS 4,535,489 A * 8/1985 Elkins ............................ 4/546
5,604,940 A * 2/1997 Shimizu ..................... 4/541.1

OTHER PUBLICATIONS

U.S. application No. 10/179,571, Shimizu, Jun. 24, 2002.

* cited by examiner

Primary Examiner—Tuan N. Nguyen
(74) Attorney, Agent, or Firm—Ladas & Parry

(57) ABSTRACT

According to the present invention, on a back surface side of a peripheral wall of a bathtub vessel formed of material having light transmittance by molding, a strip-like optical fiber which is formed into a strip shape by weaving a plurality of optical fibers in a meshy form which have end portions thereof directed to a light source of a light source device for illumination and perform the side surface illumination upon receiving an illumination light from the light source is circumferentially mounted.

9 Claims, 5 Drawing Sheets

LIGHT TRANSMITTING TYPE BATHTUB

CROSS-REFERENCE TO RELATED APPLICATION

This application is related to the pending U.S. application Ser. No. 10/179,571 filed on Jun. 24, 2002.

BACKGROUND OF THE INVENTION

1. Field of the Invention

The present invention relates to a light transmitting type bathtub which illuminates the inside of a bathtub vessel with a strip-like optical fiber which is mounted on a back surface side of a peripheral wall of the bathtub vessel having light transmittance.

2. Description of the Related Art

As a conventional bathtub, there has been generally known a bathtub which is shown in FIG. 1 as a perspective view and in FIG. 2 as a Z—Z cross-sectional view. That is, the bathtub 100 is constituted such that a rectangular bathtub vessel 101 is embedded into a floor surface 110, a semicircular chair portion 103 on which a bather sits is formed on a bottom surface 102 of the bathtub vessel 101, handles 104 which the bather grips are mounted on both sides of the bathtub vessel 101, and a headrest 105 made of rubber or the like with which a head of the bather is brought into contact is mounted on one end portion of the bathtub vessel 101. Hot water or water is supplied into the inside of the bathtub vessel 101 from a spout 106. Here, with respect to a western-style bathtub having a relatively shallow bottom, to enable a bather take a relaxed bathing posture, there has been also known a bathtub which forms a slanted surface inclined from an upper portion to a lower portion, that is, a backrest on an inner surface of a bathtub body.

However, the bathtubs having such general structures have no ideas or fail to generate the high-grade feeling.

In view of the above, recently, there has been proposed a bathtub with underwater illumination(a water light) shown in cross section in FIG. 3 which is rich in ideas by directly illuminating the inside of the bathtub using a light source. That is, in such a bathtub 200, opening portions 204 are formed in the bathtub 200 by cutting out portions of side walls 202 or a bottom wall 203 of a bathtub vessel 201 for enabling the transmission of light, transparent members 205 such as lens are adhered to inner surface of opening portions 204, and light emitting members 206 such as lamps which are turned on by a switch not shown in the drawing are mounted in the opening portions 204 whereby the inside of the bathtub vessel 201 is illuminated.

However, with respect to the bathtub 200 with underwater illumination which forms the opening portion 204 for transmitting light in the bathtub wall, there exists a fear that hot water or water leaks from these opening portions 204 or electricity leaks due to this leaking of water when the light emitting members 206 are formed of lamps, for example. Accordingly, it is necessary to provide sealing members 207 also on a back surface side of the vessel as shown in the drawing besides mounting the transparent members 205 on an inner surface side of the vessel and hence, the structure becomes complicate and pushes up a cost. Further, even when such means is provided, there still remains a possibility of leaking of water or leaking of electricity due to a fatigue generated as time lapses and hence, it is necessary to perform the maintenance and the inspection to ensure the safety always. Still further, since the lamps provide the direct illumination, it gives rise to a fatigue on eyes of a bather and hence, there have been drawbacks such as the reduction of a relaxed feeling.

SUMMARY OF THE INVENTION

The present invention has been made in view of such circumstances and it is an object of the present invention to provide a light transmitting type bathtub which is free from any fear of the leakage of water or the leakage of electricity, is free from the fatigue of eyes, etc. and is rich in ideas, and can simultaneously satisfy a mental relaxation effect which cannot be achieved by conventional bathtubs and can obtain a high-grade feeling.

The present invention is directed to a light transmitting type bathtub and the above-mentioned object of the present invention can be achieved by a light transmitting type bathtub which is characterized by circumferentially mounting a strip-like optical fiber which has an end portion thereof directed to a light source of a light source device for illumination and is formed in a strip shape by weaving a plurality of optical fibers in a meshy form which performs a side light emission upon receiving illumination light from the light source on a back surface side of a peripheral wall of a bathtub vessel formed of material having light transmittance.

Further, the above-mentioned object of the present invention can be achieved more effectively by a light transmitting type bathtub, wherein a coating is applied to a back-surface side of the bath tub vessel except for the surface corresponding to a portion where the strip-like optical fiber is circumferentially mounted.

Further, the above-mentioned object of the present invention can be achieved more effectively by a light transmitting type bathtub, wherein the light source device for illumination is configured to emit light in a plurality of colors by way of a color filter disc which is rotated.

Further, the above-mentioned object of the present invention can be achieved more effectively by a light transmitting type bathtub, wherein the end portions of strip-like optical fibers are arranged in a row and are disposed while being aligned with the rotational direction of the color filter disc.

Further, the above-mentioned object of the present invention can be achieved more effectively by a light transmitting type bathtub, wherein radially-extending masks are mounted on the color filter disc.

Further, the above-mentioned object of the present invention can be achieved more effectively by a light transmitting type bathtub, wherein the light source device for illumination is a sound-pressure control type light source device which emits light in synchronism with sound.

DESCRIPTION OF THE PREFERRED EMBODIMENTS

Contents of the present invention are explained in detail in conjunction with attached drawings which show embodiments.

Figure 1:
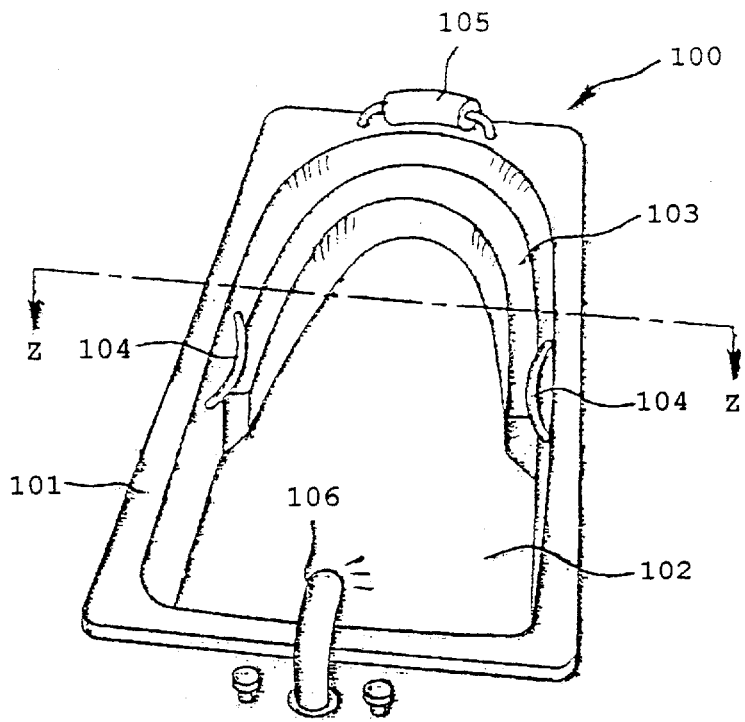
FIG. 1 is a perspective view showing the structure of a conventional general bathtub.
Figure 2:
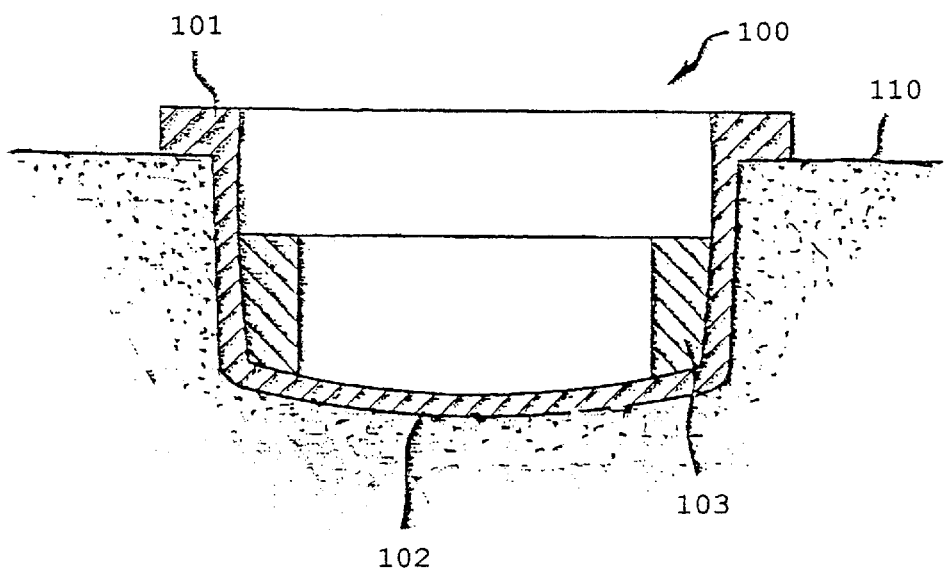
FIG. 2 is a Z—Z cross-sectional view of FIG. 1.
Figure 3:
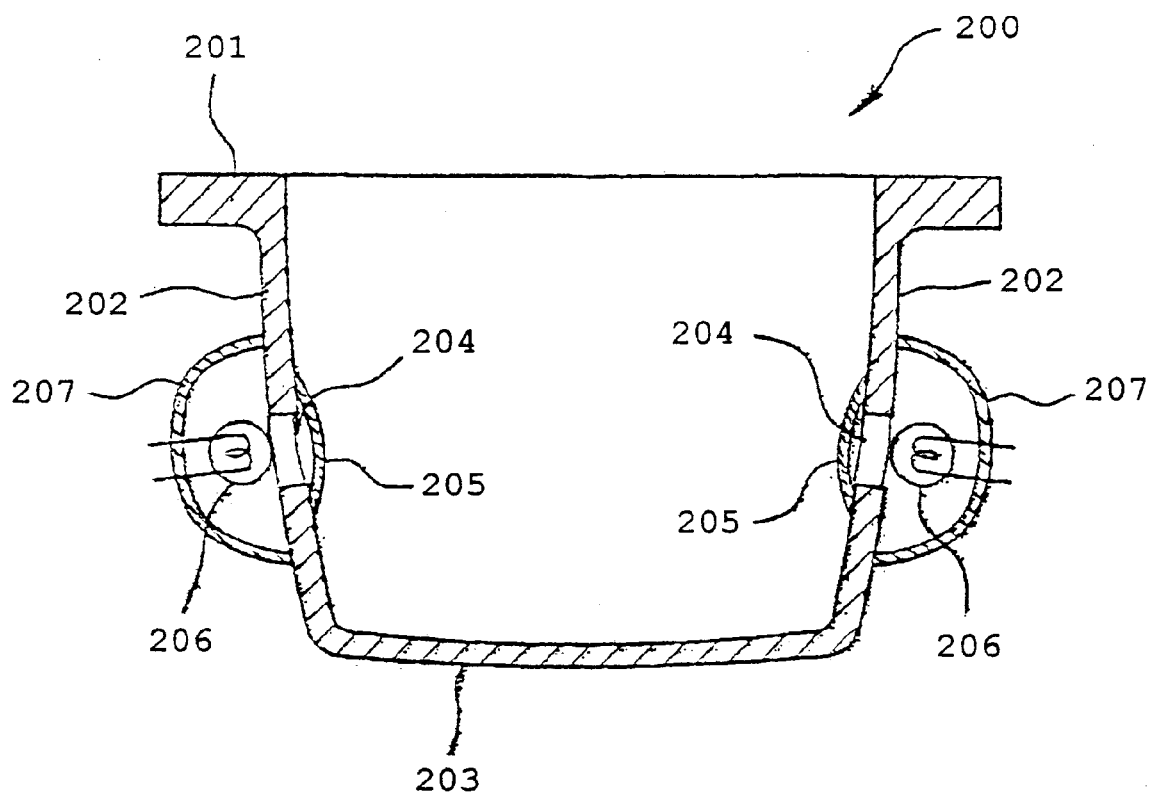
FIG. 3 is a cross-sectional view of a conventional bathtub with underwater illumination.
Figure 4:
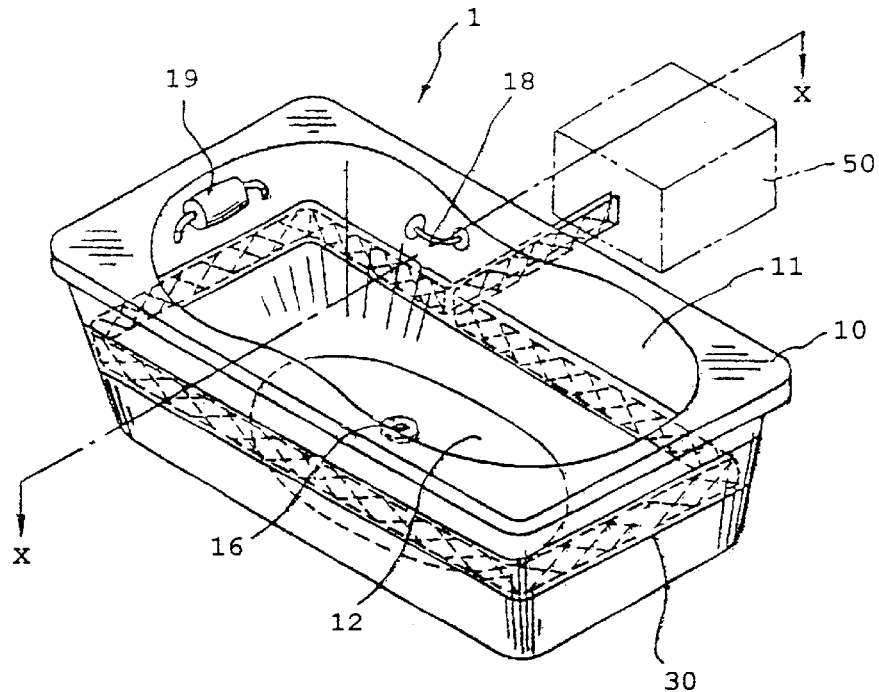
FIG. 4 is a perspective view showing one embodiment of a light transmitting type bathtub according to the present invention.
Figure 5:
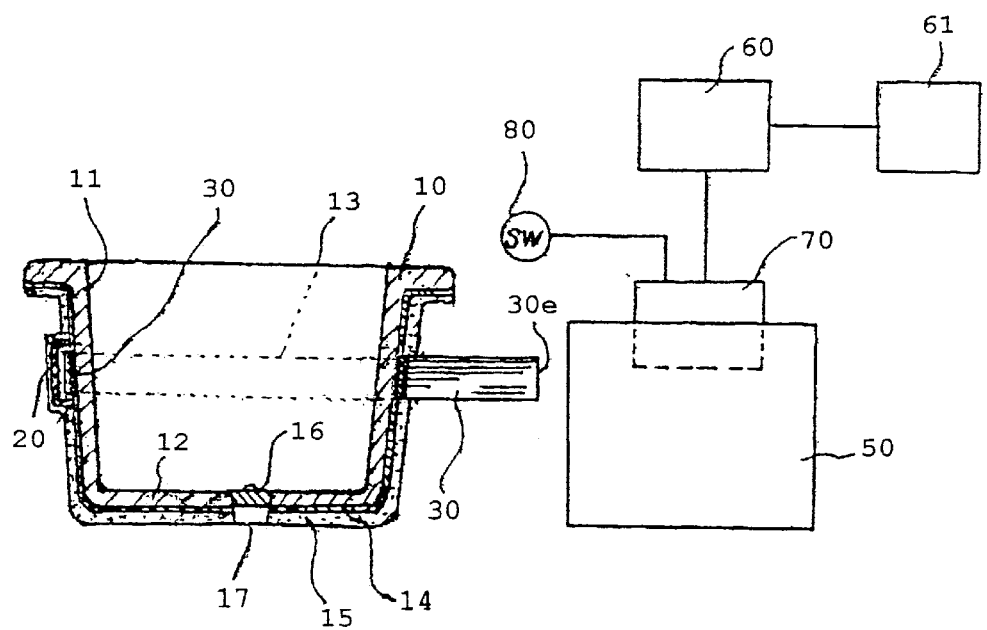
FIG. 5 is a view showing an X—X cross section of FIG. 1 and also showing the general structure of the bathtub system.

FIG. 4 is a perspective view of a light transmitting type bathtub 1 according to one embodiment of the present invention (hereinafter referred to as "the bathtub") and FIG. 5 is a view which shows an X—X cross section and shows a system of the whole bathtub 1. As shown in these drawings, the bathtub 1 is substantially comprised of a bathtub vessel 10 which stores hot water therein, a strip-like optical fiber 30 which is circumferentially mounted on the bathtub vessel 10 and emits light, a light source device 50 for illumination which supplies an illumination light to the strip-like optical fiber 30, a sound generation device 60, a speaker 61 which delivers the sound in the inside of a bathroom, a control device 70 which controls the light source device 50, and a manipulation switch 80 which turns on or off the driving of the light source device 50 by way of the control device 70.

The bathtub vessel 10 is constituted of a peripheral wall 11 and a bottom wall 12. The peripheral wall 11 and the bottom wall 12 have a thickness of approximately 5 mm, for example, and are formed of transparent or semitransparent plastic material having light transmittance such as acrylic resin or methaacrylate resin by molding. To a back-surface side of the peripheral wall 11, a coating film 14 formed of a white gel coat is applied by spraying except for a strip-like portion 13 which surrounds the peripheral wall 11 in a strip form. Further, on an outer surface of the coating film 14, a known FRP (Fiber Reinforced Plastic) layer 15 formed by solidifying glass fiber with resin is formed. The strip-like portion 13 includes a strip-like optical fiber 30 which has an end portion 30e thereof directed to a light source of the light source device 50 and performs a side-surface light emission upon receiving illumination light from the light source. Further, the bottom wall 12 is provided with a drain opening 17 which is opened or closed by a plug 16. Here, although a handle 18 and a headrest 19 are attached to the inside of the peripheral wall 11 in this embodiment, these components are suitably provided when necessary. Further, although the shape of the whole bathtub vessel 10 is formed in a rectangular shape, it is needless to say that the design of the shape is suitably changed to an elliptical shape or the like, for example depending a request.

As shown in FIG. 5, the strip-like optical fiber 30 is circumferentially mounted on the strip-like portion 13 of the peripheral wall 11 where the back-surface side coating film 14 is not formed, that is, a portion where the strip-like optical fiber 30 is circumferentially mounted, so that an illumination light emitted from a side-surface of the strip-like optical fiber 30 is irradiated to the inside of the bathtub vessel 10 by passing through the peripheral wall 11. Here, the color of the coating film 14 is not limited to white and can be selected to an arbitrary color such as ivory or silver when necessary.

Figure 6:
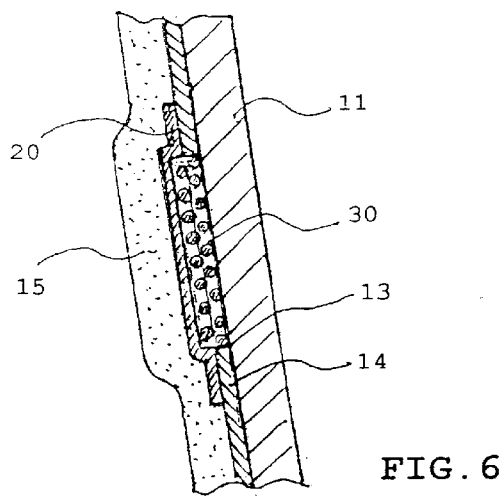
FIG. 6 is a partially enlarged cross-sectional view of FIG. 5.
Figure 7:
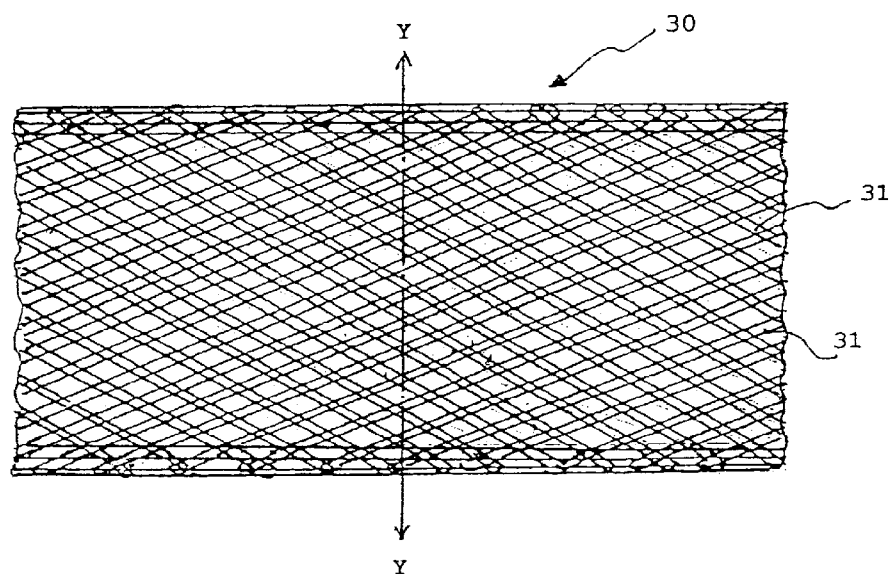
FIG. 7 is a plan view showing one example of a strip-like optical fiber which constitutes an essential part of the present invention.
Figure 8:
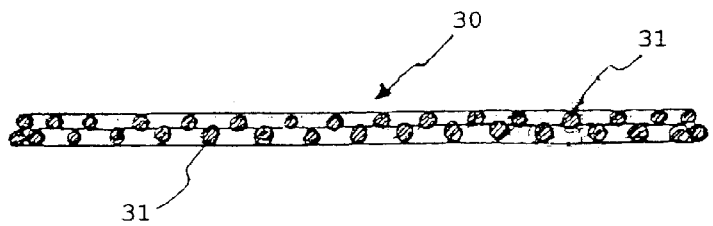
FIG. 8 is a Y—Y cross-sectional view of FIG. 7.

FIG. 6 is a view which shows the manner of circumferentially mounting the strip-like optical fiber 30 in detail by partially enlarging a cross-section of FIG. 5. As shown in the drawing, the strip-like optical fiber 30 is disposed along the strip-like portion 13 which is disposed such that the strip-like portion 13 surrounds the back-surface side of the peripheral wall 11. The strip-like optical fiber 30 is adhered to the peripheral wall 11 using an adhesive agent or the like when necessary and, thereafter, is held by a strip-like cover 20 from the outside thereof. Further, an outer side of the strip-like cover 20 is covered with the FRP layer 15 having a thickness of approximately 5 mm, for example. The strip-like optical fiber 30 is formed into a strip-like structure by weaving a plurality (33 pieces in total in this embodiment) of optical fibers 31 which perform the side-surface light emission in a meshy form using a technique of "Nishijin brocade" (one meshy type in Japan), for example, as shown in a plan view of FIG. 7 and a Y—Y cross-sectional view of FIG. 8. The end portions 31e (both end portions consisting of distal end portions 31e1 and proximal end portions 31e2) of respective optical fibers 31 are disposed such that they are directed toward the light source of the light source device 50 as described later based on FIG. 9.

Here, it is preferable to set the position where the strip-like optical fiber 30 is circumferentially mounted on the peripheral wall 11 at a position more or less above a usual water level of hot water stored in the bathtub vessel 10 in view of the fact that the illumination light is reflected on a surface of the hot water. In this manner, since the strip-like optical fiber 30 is mounted on the back surface side of the peripheral wall 11, with respect to the bathtub 1, there is no fear of the leaking of water or the leaking of electricity caused by the leaking of water which has occurred in the conventional bathtub.

Figure 9:
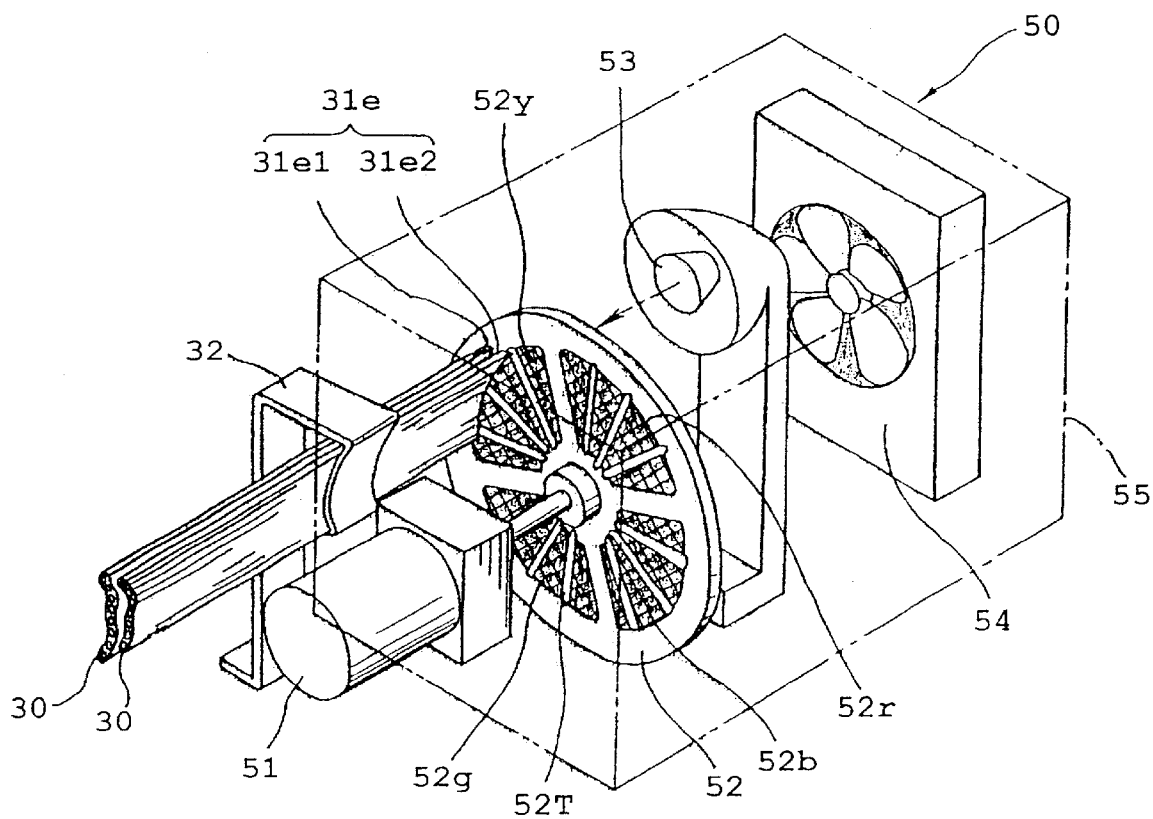
FIG. 9 is a perspective view showing one example of an illumination device which constitutes an essential part of the present invention.

Subsequently, the light source device 50 is, as shown in a perspective view of FIG. 9, comprised of a color filter disc 52 which is rotated by a motor 51, a halogen lamp 53 which irradiates the illumination light to the disc 52, a cooling fun 54 and a box 55 which houses these appliances(indicated by a phantom line). Although the above-mentioned control device 70 is also mounted in the inside of the box 55, the control device 70 is omitted from the drawing. The end portions 31e (distal end portions 31e1 and proximal end portions 31e2) of respective optical fibers 31 are respectively arranged in a row and are held by a folder 32 such that the end portions 31e are arranged to be aligned with the rotational direction of the color filter disc 52.

The color filter disc 52 is formed by mounting filters of four colors consisting of a red filter 52r, a blue filter 52b, a green filter 52g and a yellow filter 52y in gap portions respectively formed in the disc in an extended form. Further, as shown in the drawing, to each filter, a plurality of strip-like aluminum tapes 52T are laminated in the radial direction with an approximately equidistant gap thus covering each filter with a radially-extending mask. The color filter disc 52 having the above-mentioned constitution is rotated at a given speed by the motor 51 driven by way of the control device 70 when the switch 80 is turned on. Here, the fun 54 is also driven at the same time and the halogen lamp 53 is also simultaneously turned on and the illumination light is irradiated to the rotating color filter disc 52.

The speaker 61 is disposed in the inside of the bathroom in which the bathtub 1 is installed or in the vicinity of the bathtub. The speaker 61 is connected to the sound generation device 60 such as a radio cassette player or a tape recorder or a cable broadcasting, for example, so that the sound such as music transmitted from the sound generation device 60 is floated into the inside of the bathroom.

The control device 70 drives the above-mentioned respective appliances in the inside of the light source device 50 by turning on the switch 80. Here, the control device 70 is configured to pick up the sound pressure of the sound generation device 60 and control the illuminance of the halogen lamp 53 and the rotational speed of the motor 51 and the like to desired values in synchronism with the sound pressure. In this manner, this embodiment adopts a sound pressure control method in the light source device 50. Here, since such a constitution is well known in the field to which the present invention pertains, the detailed explanation is omitted.

Subsequently, the manner of operation and advantageous effects of the bathtub 1 having the above-mentioned constitution is explained. First of all, at the time of bathing, a bather stores hot water in the bathtub vessel 10 and turns on the switch 80 after elevating the temperature of the hot water to an appropriate temperature. Due to such an operation, the motor 51 disposed in the inside of the light source device 50 is initiated so that the color filter disc 52 starts the rotation thereof. Simultaneously, the cooling fan 54 is driven and the halogen lamp 53 is turned on so as to sequentially illuminate the color filters 52r, 52b, 52g, 52y of the rotating color filter disc 52. Here, the sound such as music is floated out from the speaker 61 into the inside of the bathroom and the illuminance of the halogen lamp 53 and the rotational speed of the motor 51 are controlled to desired values by the control device 70 in synchronism with the sound pressure of the sound generation device 60.

When the light is irradiated to the color filters 52r, 52b, 52g, 52y of the color filter disc 52, the irradiated light passes through gaps between the linear masks formed of the aluminum tapes 52T formed on these respective filters, and is sequentially incident on one-end side of the end portions 31e (distal end portions 31e1, proximal end portions 31e2) of respective optical fibers 31 which are arranged in a row while being aligned with the rotational direction of the color filter disc 52. In this manner, when the light is incident on the end portions 31e of respective optical fibers 31 which form the strip-like optical fiber 30, the light sequentially illuminates in respective colors of red, blue, green, yellow in the process in which the light is transmitted in a plurality of respective optical fibers 31 (33 pieces) and the inside of the bathtub is illuminated with these colors.

This illumination light is an indirect illumination light and hence, the illumination light is gentle to eyes of the bather. Further, the illumination light emits light in the wave state by way of the strip-like optical fiber 30 and the illuminance is changed in synchronism with the sound pressure of the sound floated into the inside of the bathroom and hence, the bather perceives images of fantasy as if he watches the wave of a moving rainbow whereby the bather can enjoy the bathing in an extremely relaxed feeling. Particularly, when the bather takes a bath while decreasing the illuminance in the inside of the bathroom, the illumination light reflects on the hot water and shines brightly so that the bathtub can obtain the more sophisticated high-grade feeling.

Further, when the bather takes a bath in the state that tranquil mood music is floated out from the speaker 61, the bather can take a bath in a relaxed posture in the calm atmosphere so that the physical fatigue recovery effect can be enhanced.

As has been described heretofore, according to the bathtub 1, there is no fear of the leaking of water and the leaking of electricity caused by the leaking of water structurally. Further, since the illumination light is an indirect illumination, the illumination light is gentle to the eyes of the bather. Further, the bathtub 1 is rich in ideas. Accordingly, the bathtub 1 can obtain the high-grade feeling and the high-grade mental relaxation effect.

Although the content of the present invention has been explained based on one embodiment heretofore, the present invention is not always limited to such an embodiment and following various modifications are available with respect to the constitution of the present invention.

First of all, although the strip-like optical fiber 30 is formed by weaving a plurality of optical fibers 31, the number of using optical fibers 31 and the weaving method of the using optical fibers 31 can be freely selected. For example, the optical fibers 31 are woven in a spiral form or in a mountain-like form. It is also possible to set the position where the strip-like optical fiber 30 is circumferentially mounted on the peripheral wall 11 below the water level of the hot water stored in the water vessel 10. By mounting the strip-like optical fiber 30 at such a position, the illumination light is directly irradiated to the hot water and hence, an advantageous effect that the bather can watch the whole hot water which shines and twinkles beautifully is obtained.

Further, the light source of the light source device 50 for illumination is not limited to the halogen lamp 53 and various lamps including an LED(Light Emitting Diode) and a fluorescent lamp are applicable. Although four colors consisting of red, blue, green and yellow are selected as the light source colors by way of the color filter disc 52, it is needless to say that the kinds can be increased or decreased when necessary. Further, although it is preferable to mount the radially-extending masks formed of the aluminum tapes 52T on respective color filters of the color filter disc 52, it is possible to provide no masks to these color filters.

Still further, although the above-mentioned embodiment adopts the light source device which is controlled in response to the sound pressure as the light source device 50, the embodiment can adopt images(moving images), light (illumination light in the bathroom) or the like in place of the sound. Further, from a viewpoint of cost, a case in which the embodiment eliminates such control sources is also sufficiently conceivable.

As has been explained in detail heretofore, according the light transmitting bathtub of the present invention, since the illumination means which illuminates the inside of the bathtub is mounted on the back surface side of the bathtub vessel, there is no fear of the leaking of water or the leaking of electricity caused by the leaking of water. Further, since the illumination light is the indirect illumination, the illumination light is gentle to the eyes of the bather. Still further, since the light transmitting bathtub adopts the idea such that the illumination light is irradiated with brilliant colors in the wave state, the bather can enjoy the bathing while deeply perceiving the high-grade feeling.

Particularly, when the light source device for illumination adopts the sound pressure control method, the bather can take a bath with abundant colorful hot water while listening to the mood music and hence, it is possible to remarkably enhance the physical fatigue recovery effect in addition to the mental relaxation effect.

What is claimed is:

1. A light transmitting type bathtub characterized by circumferentially mounting a strip-like optical fiber which has an end portion thereof directed to a light source of a light source device for illumination and is formed in a strip shape by weaving a plurality of optical fibers in a meshy form which perform a side light emission upon receiving illumination light from said light source on a back surface side of a peripheral wall of a bathtub vessel formed of material having light transmittance.

2. A light transmitting type bathtub according to claim 1, wherein a coating is applied to said back-surface side surface of said bath tub vessel except for said surface corresponding to a portion where said strip-like optical fiber is circumferentially mounted.

3. A light transmitting type bathtub according to claim 1, wherein an FRP layer formed by solidifying glass fiber with resin is formed on an internal surface of said bathtub.

4. A light transmitting type bathtub according to claim 1, wherein said light source device for illumination is configured to emit light in a plurality of colors by way of a color filter disc which is rotated.

5. A light transmitting type bathtub according to claim 4, wherein said end portions of strip-like optical fibers are arranged in a row and are disposed while being aligned with the rotational direction of said color filter disc.

6. A light transmitting type bathtub according to claim 5, wherein radially-extending masks are mounted on said color filter disc.

7. A light transmitting type bathtub according to claim 4, wherein said light source device for illumination is a sound-pressure control type light source device which emits light in synchronism with sound.

8. A light transmitting type bathtub according to claim 1, wherein said meshy form is a Nishijin brocade.

9. A light transmitting type bathtub according to claim 1, wherein said light source device for illumination is a sound-pressure control type light source device which emits light in synchronism with sound.

* * * * *